US006794871B2

(12) United States Patent
Imai et al.

(10) Patent No.: US 6,794,871 B2
(45) Date of Patent: Sep. 21, 2004

(54) MAGNETIC RESONANCE MAGNET SYSTEM AND IMAGING APPARATUS WITH EXTENDABLE PATIENT SUPPORT ARMS

(75) Inventors: Akira Imai, Tokyo (JP); Masaaki Sakuma, Tokyo (JP); Akira Izuhara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/256,749

(22) Filed: Sep. 27, 2002

(65) Prior Publication Data

US 2003/0062898 A1 Apr. 3, 2003

(30) Foreign Application Priority Data

Sep. 28, 2001  (JP) ........................................ 2001-300376

(51) Int. Cl.⁷ ............................ G01V 3/00; G01R 33/20
(52) U.S. Cl. ........................................ 324/318; 324/322
(58) Field of Search ............................... 324/300–322; 600/407–423

(56) References Cited

U.S. PATENT DOCUMENTS

| 4,773,637 | A |   | 9/1988  | Jarin |
| 4,968,937 | A | * | 11/1990 | Akgun ........................ 324/318 |
| 5,272,776 | A |   | 12/1993 | Kitamura |
| 5,735,278 | A | * | 4/1998  | Hoult et al. ................ 600/422 |
| 6,092,248 | A |   | 7/2000  | Boemmel et al. |
| 6,246,239 | B1 | * | 6/2001 | Krogmann et al. ......... 324/318 |
| 6,256,528 | B1 |   | 7/2001 | Zonneveld et al. |
| 6,381,780 | B1 |   | 5/2002 | Nose et al. |
| 2003/0062898 | A1 | * | 4/2003 | Imai et al. .................. 324/318 |

* cited by examiner

*Primary Examiner*—Diego Gutierrez
*Assistant Examiner*—Tiffany A. Fetzner
(74) *Attorney, Agent, or Firm*—Carl B. Horton, Esq.; Armstrong Teasdale LLP (57) ABSTRACT

For the purpose of always keeping the positional relationship fixed between a support section for supporting a supported object and a base section for receiving the support section, the present apparatus comprises: a support section 500 for horizontally supporting a supported object; a base section 112 having a horizontal plane on its top; and a position adjusting section 300 provided between the support section and the base section, for moving the support section forward/backward between a position above the horizontal plane and a position off the horizontal plane while keeping the support section at a level higher than the horizontal plane, and for moving the support section upward/downward between a position higher than the horizontal plane and a position lower than the horizontal plane at the position off the horizontal plane.

13 Claims, 10 Drawing Sheets

MAGNETIC RESONANCE MAGNET SYSTEM AND IMAGING APPARATUS WITH EXTENDABLE PATIENT SUPPORT ARMS

CROSS REFERENCE TO RELATED APPLICATIONS

This application claims the benefit of Japanese Application No. 2001-300376 filed Sep. 28, 2001.

BACKGROUND OF THE INVENTION

The present invention relates to a support apparatus, magnet system and magnetic resonance imaging apparatus, and particularly to a support apparatus capable of placing a support plate, which horizontally supports a supported object, either over a base or off the base, a magnet system for a magnetic resonance imaging apparatus comprising such a support apparatus, and a magnetic resonance imaging apparatus comprising such a magnet system.

In a magnetic resonance imaging (MRI) apparatus, a subject to be imaged is carried into an internal space of a magnet syster i.e., an imaging space; a static magnetic field, gradient magnetic fields and a high frequency magnetic field are applied to excite spins within the subject to generate magnetic resonance signals; and an image is reconstructed based on the received signals.

One type of the magnet system is the open magnet system. The open magnet system has a structure in which a pair of magnets vertically facing each other across the imaging space are supported by a C-shaped yoke. The magnet system having such a structure provides high openness because the vertical yoke is disposed only on one side.

The subject to be imaged is carried into the imaging space of such a magnet system, being rested on a movable bed having wheels. The carrying is achieved by horizontal movement of the movable bed from the front of the magnet system. Such a carrying scheme facilitates access to the subject during imaging, and allows efficient use of the internal space of the magnet system.

In the MRI apparatus employing the movable bed to carry the subject into the imaging space as described above, the bed for supporting the subject and the magnet system for receiving the bed are separate. Therefore, the positional relationship between the bed and the magnet system while receiving the bed is not fixed.

SUMMARY OF THE INVENTION

It is therefore an object of the present invention to provide a support apparatus in which the positional relationship between a support section for supporting a supported object and a base section for receiving the support section is always fixed, a magnet system comprising such a support apparatus, and a magnetic resonance imaging apparatus comprising such a magnet system.

(1) The present invention, in accordance with one aspect thereof for solving the aforesaid problem, is a support apparatus characterized in comprising: a support section for horizontally supporting a supported object; a base section having a horizontal plane on its top; and a position adjusting section provided between said support section and said base section, for moving said support section forward/backward between a position above said horizontal plane and a position off said horizontal plane while keeping said support section at a level higher than said horizontal plane, and for moving said support section upward/downward between a position higher than said horizontal plane and a position lower than said horizontal plane at said position off said horizontal plane.

(2) The present invention, in accordance with another aspect thereof for solving the aforesaid problem, is a magnet system for a magnetic resonance imaging apparatus that has a space for receiving a subject to be imaged and generates a static magnetic field, gradient magnetic field and high frequency magnetic field in said space, characterized in comprising: a base section having a horizontal plane on its top; a post section provided on one side of said base section and extending upright beyond said horizontal plane; a hood section supported by said post section, facing said horizontal plane across said space; a support section for horizontally supporting the subject to be imaged; and a position adjusting section provided between said base section and said support section, for moving said support section forward/backward between a position above said horizontal plane and a position off said horizontal plane on the other side of said base section while keeping said support section at a level higher than said horizontal plane, and for moving said support section upward/downward between a position higher than said horizontal plane and a position lower than said horizontal plane at said position off said horizontal plane.

(3) The present invention, in accordance with still another aspect thereof for solving the aforesaid problem, is a magnetic resonance imaging apparatus having: a magnet system that has a space for receiving a subject to be imaged and generates a static magnetic field, gradient magnetic field and high frequency magnetic field in said space; and image producing means for producing an image based on magnetic resonance signals acquired through said magnet system, characterized in that said magnet system comprises: a base section having a horizontal plane on its top; a post section provided on one side of said base section and extending upright beyond said horizontal plane; a hood section supported by said post section, facing said horizontal plane across said space; a support section for horizontally supporting the subject to be imaged; and a position adjusting section provided between said base section and said support section, for moving said support section forward/backward between a position above said horizontal plane and a position off said horizontal plane on the other side of said base section while keeping said support section at a level higher than said horizontal plane, and for moving said support section upward/downward between a position higher than said horizontal plane and a position lower than said horizontal plane at said position off said horizontal plane.

In the present invention of the aspects as described regarding (1)–(3), a position adjusting section for moving the support section forward/backward between a position above a horizontal plane at the top of the base section and a position off the horizontal plane while keeping the support section at a level higher than the horizontal plane, and for moving the support section upward/downward between a position higher than the horizontal plane and a position lower than the horizontal plane at the position off the horizontal plane, is provided between the base section and the support section; and therefore, the positional relationship between the support section and the base section for receiving it can be always fixed.

Preferably, said position adjusting section comprises a pair of link mechanisms respectively provided between two positions of said support section along a direction parallel with said horizontal plane and perpendicular to the direction of said forward/backward movement and the corresponding end portions of said base section, said link mechanisms being pivotally rotatable relative to said base section; and a movement mechanism for moving a portion of said pair of link mechanisms adjacent to said base section in the direction of said forward/backward movement, so that the position adjustment of the support section can be suitably achieved.

Preferably, each member of said pair of link mechanisms comprises a pair of arms configured to avoid mutual interference involved in said pivotal rotation so that the upward/downward movement can be suitably achieved.

(4) The present invention, in accordance with still another aspect thereof for solving the aforesaid problem, is a support apparatus characterized in comprising: a support section for horizontally supporting a supported object; a base section having a horizontal plane on its top; and a position adjusting section provided between said support section and said base section, for moving said support section forward/backward between a position above said horizontal plane and a position off said horizontal plane while keeping said support section at a level higher than said horizontal plane.

(5) The present invention, in accordance with still another aspect thereof for solving the aforesaid problem, is a magnet system for a magnetic resonance imaging apparatus that has a space for receiving a subject to be imaged and generates a static magnetic field, gradient magnetic field and high frequency magnetic field in said space, characterized in comprising: a base section having a horizontal plane on its top; a post section provided on one side of said base section and extending upright beyond said horizontal plane; a hood section supported by said post section, facing said horizontal plane across said space; a support section for horizontally supporting the subject to be imaged; and a position adjusting section provided between said base section and said support section, for moving said support section forward/backward between a position above said horizontal plane and a position off said horizontal plane on the other side of said base section while keeping said support section at a level higher than said horizontal plane.

(6) The present invention, in accordance with still another aspect thereof for solving the aforesaid problem, is a magnetic resonance imaging apparatus having: a magnet system that has a space for receiving a subject to be imaged and generates a static magnetic field, gradient magnetic field and high frequency magnetic field in said space; and image producing means for producing an image based on magnetic resonance signals acquired through said magnet system, characterized in that said magnet system comprises: a base section having a horizontal plane on its top; a post section provided on one side of said base section and extending upright beyond said horizontal plane; a hood section supported by said post section, facing said horizontal plane across said space; a support section for horizontally supporting the subject to be imaged; and a position adjusting section provided between said base section and said support section, for moving said support section forward/backward between a position above said horizontal plane and a position off said horizontal plane on the other side of said base section while keeping said support section at a level higher than said horizontal plane.

In the present invention of the aspects as described regarding (4)–(6), a position adjusting section for moving the support section forward/backward between a position above a horizontal plane at the top of the base section and a position off the horizontal plane while keeping the support section at a level higher than the horizontal plane, is provided between the support section and the base section; and therefore, the positional relationship between the support section and the base section for receiving it can be always fixed.

Preferably, said position adjusting section comprises a pair of extendable arms respectively provided between two positions of said support section along a direction parallel with said horizontal plane and perpendicular to the direction of said forward/backward movement and the corresponding end portions of said base section, said extendable arms being capable of extending relative to said base section, so that the forward/backward movement of the support section can be suitably achieved.

Preferably, said position adjusting section comprises a pair of arms respectively provided between two positions of said support section along a direction parallel with said horizontal plane and perpendicular to the direction of said forward/backward movement and the corresponding end portions of said base section; and a movement mechanism for enabling a portion of said support arms adjacent to said base section to move in the direction of said forward/backward movement, so that the forward/backward movement of the support section can be suitably achieved.

Therefore, the present invention can provide a support apparatus in which the positional relationship between a support section for supporting a supported object and a base section for receiving the support section is always fixed, a magnet system comprising such a support apparatus, and a magnetic resonance imaging apparatus comprising such a magnet system.

Further objects and advantages of the present invention will be apparent from the following description of the preferred embodiments of the invention as illustrated in the accompanying drawings.

DETAILED DESCRIPTION OF THE INVENTION

Figure 1:
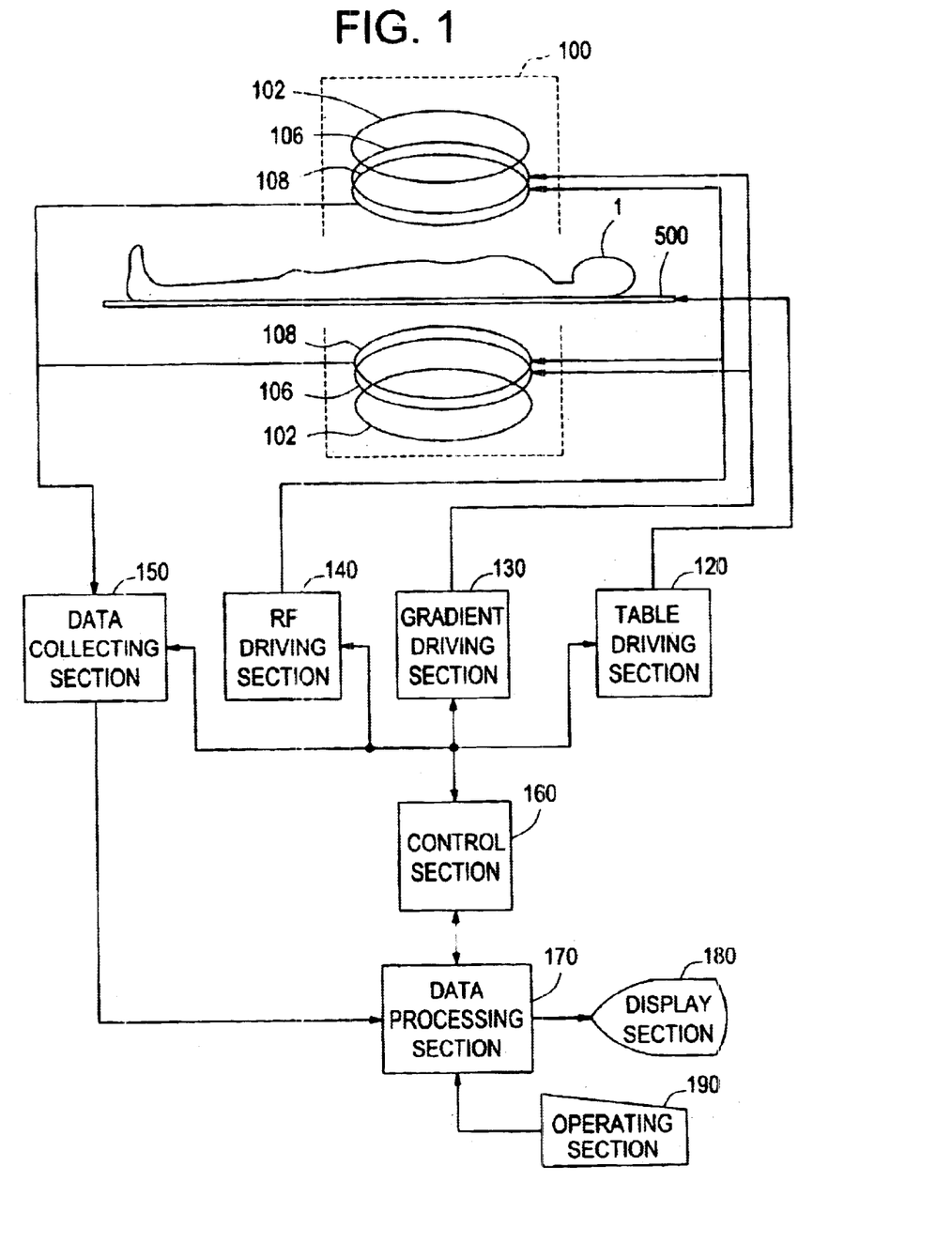
FIG. 1 is a block diagram of an apparatus in accordance with one embodiment of the present invention.

Several embodiments of the present invention will now be described in detail with reference to the accompanying drawings. It should be noted that the present invention is not limited to the embodiments. FIG. 1 shows a block diagram of a magnetic resonance imaging apparatus, which is one embodiment of the present invention. The configuration of the apparatus represents an embodiment of the apparatus in accordance with the present invention.

As shown in FIG. 1, the present apparatus has a magnet system 100. The magnet system 100 has a main magnetic field magnet section 102, a gradient coil section 106 and an RF coil section 108. The main magnetic field magnet section 102, gradient coil section 106 and RF coil section 108 each comprise a pair of members facing each other across a space. These sections have a generally disk-like shape and are disposed to have a common center axis. The magnet system 100 will be described in detail later.

A subject 1 is rested on a table 500 and carried into and out of the internal space (bore) of the magnet system 100. The table 500 is driven by a table driving section 120. The relationship between the table 500 and the magnet system 100 will be described in detail later.

The main magnetic field magnet section 102 generates a static magnetic field in the internal space of the magnet system 100. The direction of the static magnetic field is generally orthogonal to the direction of the body axis of the subject 1. That is, a "vertical" magnetic field is generated. The main magnetic field magnet section 102 is constructed using a permanent magnet, for example. It will be easily recognized that the main magnetic field magnet section 102 is not limited to a permanent magnet, but may be made using a super or normal conductive electromagnet or the like.

The gradient coil section 106 generates three gradient magnetic fields for imparting respective gradients to the static magnetic field strength in directions of three mutually perpendicular axes, ie., slice axis, phase axis and frequency axis.

The gradient magnetic field in the slice axis direction is sometimes referred to as the slice gradient magnetic field. The gradient magnetic field in the phase axis direction is sometimes referred to as the phase encoding gradient magnetic field. The gradient magnetic field in the frequency axis direction is sometimes referred to as the readout gradient magnetic field. In order to enable generation of such gradient magnetic fields, the gradient coil section 106 has three gradient coils, which are not shown. The gradient magnetic field will be sometimes referred to simply as the gradient hereinbelow.

The RF coil section 108 transmits an RF (radio frequency) pulse for exciting spins within the subject 1 in the static magnetic field space. The RF coil section 108 also receives magnetic resonance signals generated by the excited spins. The RF coil section 108 may be a type that conducts transmission and reception by the same coil or by separate coils.

The gradient coil section 106 is connected with a gradient driving section 130. The gradient driving section 130 supplies driving signals to the gradient coil section 106 to generate the gradient magnetic fields. The gradient driving section 130 has three driving circuits, which are not shown, corresponding to the three gradient coils in the gradient coil section 106.

The RF coil section 108 is connected with an RF driving section 140. The RF driving section 140 supplies driving signals to the RF coil section 108 to transmit the RF pulse, thereby exciting the spins within the subject 1.

The RF coil section 108 is connected to a data collecting section 150. The data collecting section 150 gathers receive signals received by the RF coil section 108 by sampling them, and collects the signals as digital data.

The table driving section 120, gradient driving section 130, RF driving section 140 and data collecting section 150 are connected with a control section 160. The control section 160 controls the table driving section 120, gradient driving section 130, RF driving section 140 and data collecting section 150 to carry out imaging.

The control section 160 is constructed using, for example, a computer. The control section 160 has a memory, which is not shown. The memory stores programs for the control section 160 and several kinds of data. The function of the control section 160 is achieved by the computer executing a program stored in the memory.

The output of the data collecting section 150 is connected to a data processing section 170. The data collected by the data collecting section 150 is input to the data processing section 170. The data processing section 170 is constructed using, for example, a computer. The data processing section 170 has a memory, which is not shown. The memory stores programs for the data processing section 170 and several kinds of data.

The data processing section 170 is connected to the control section 160. The data processing section 170 is above the control section 160 and controls it. The function of the present apparatus is achieved by the data processing section 170 executing a program stored in the memory.

The data processing section 170 stores data collected by the data collecting section 150 into the memory. A data space is formed in the memory. The data space constitutes a two-dimensional Fourier space. The Fourier space will be sometimes referred to as a k-space hereinbelow. The data processing section 170 performs a two-dimensional inverse Fourier transformation on the data in the k-space to reconstruct an image of the subject 1. The data processing section 170 is an embodiment of the image producing means of the present invention.

The data processing section 170 is connected with a display section 180 and an operating section 190. The display section 180 comprises a graphic display, etc. The operating section 190 comprises a keyboard, etc., provided with a pointing device.

The display section 180 displays the reconstructed image and several kinds of information output from the data processing section 170. The operating section 190 is operated by a user, and the section 190 inputs several commands, information and so forth to the data processing section 170. The user interactively operates the present apparatus via the display section 180 and operating section 190.

Figure 2:
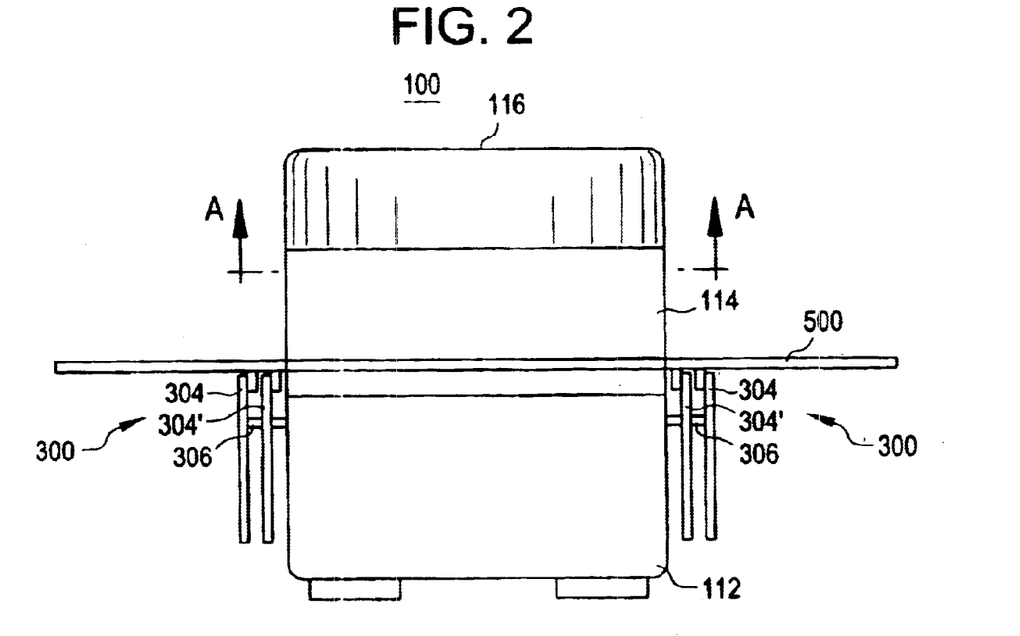
FIG. 2 is a schematic view showing the configuration of a magnet system.
Figure 3:
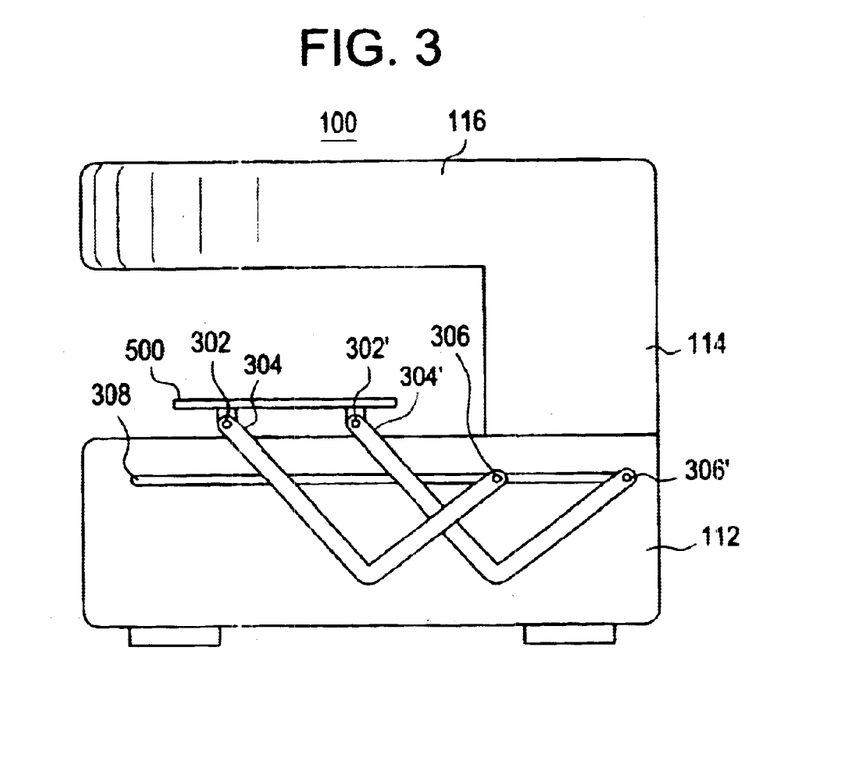
FIG. 3 is a schematic view showing the configuration of the magnet system.
Figure 4:
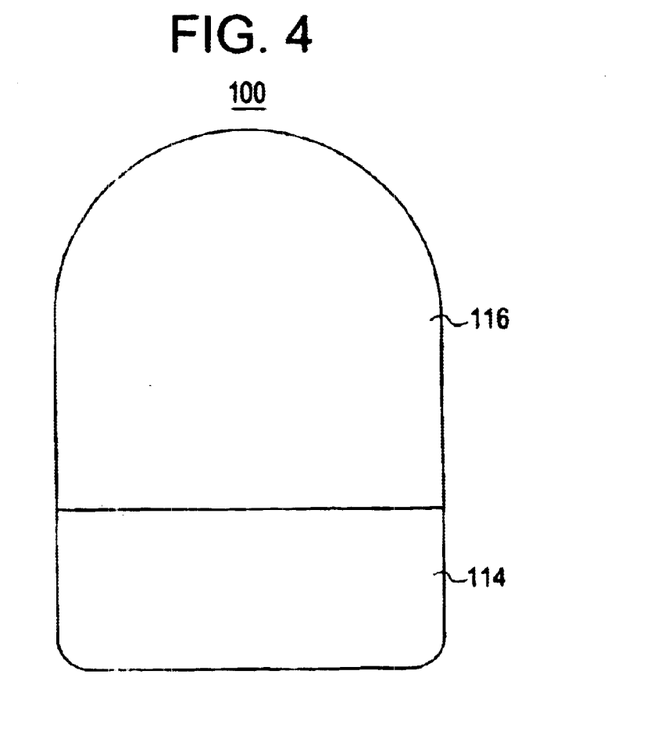
FIG. 4 is a schematic view showing a cross section taken along a line A—A in FIG. 3.

FIGS. 2, 3 and 4 schematically show the configuration of the magnet system 100. FIG. 2 is a front elevational view, FIG. 3 is a right side view and FIG. 4 is a cross section taken along a line A—A in FIG. 2. Although not shown, a left side view corresponds to a mirror image of FIG. 3. As shown, the magnet system 100 has a base section 112, a post section 114 and a hood section 116.

The base section 112 is an embodiment of the base section in accordance with the present invention. The post section 114 is an embodiment of the post section in accordance with the present invention. The hood section 116 is an embodiment of the hood section in accordance with the present invention.

The upper surface of the base section 112 forms a horizontal plane. The post section 114 stands generally upright in the depth of the base section 112 as viewed from the front. The hood section 116 extends generally horizontally from the upper portion of the post section 114 toward the front. The lower surface of the hood section 116 faces the upper surface of the base section 112 across a space.

Figure 5:
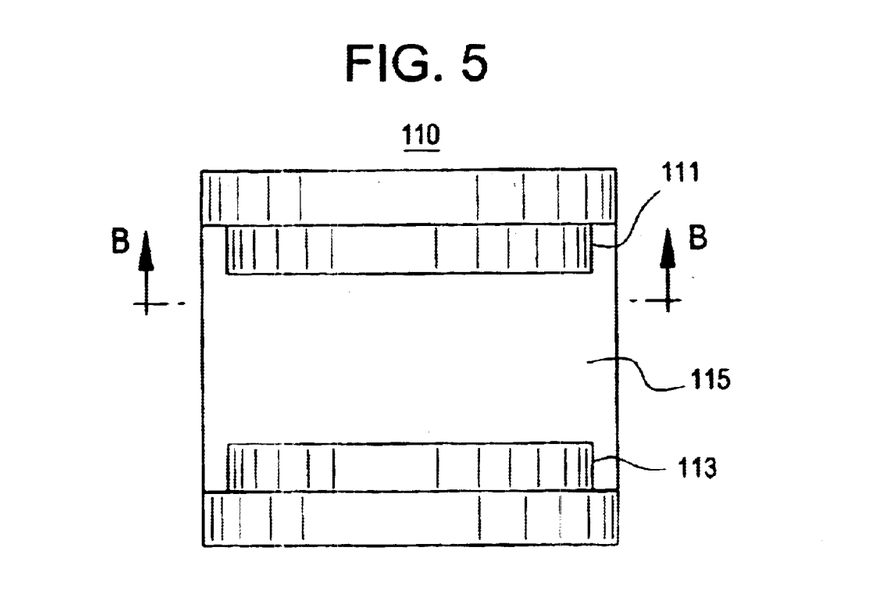
FIG. 5 is a schematic view showing the configuration of a magnet body.
Figure 6:
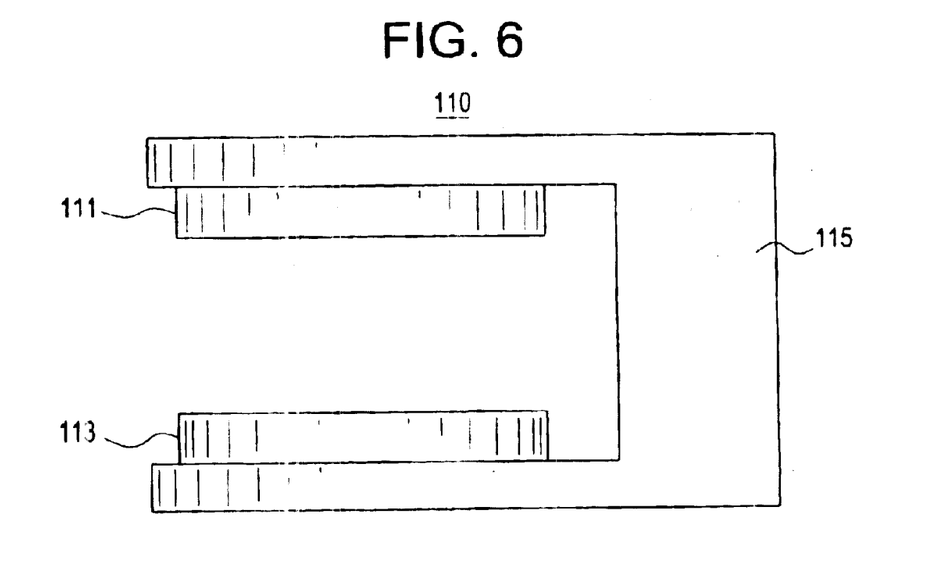
FIG. 6 is a schematic view showing the configuration of the magnet body.
Figure 7:
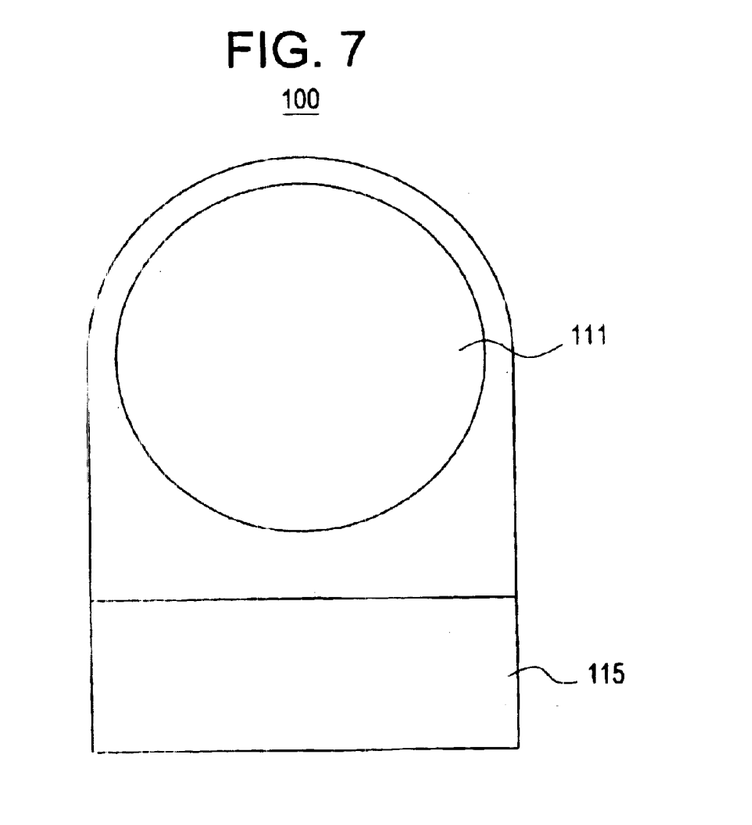
FIG. 7 is a schematic view showing a cross section taken along a line B—B in FIG. 6.

The magnet system incorporates a magnet body. FIGS. 5, 6 and 7 schematically show the configuration of the magnet body 110. FIG. 5 is a front elevational view, FIG. 6 is a right side view and FIG. 7 is a cross section taken along a line B—B in FIG. 5. Although not shown, a left side view corresponds to a mirror image of FIG. 6. As shown, the magnet body 110 has an upper magnetic pole section 111, a lower magnetic pole section 113 and a yoke 115.

The yoke 115 has a generally C-shape structure as viewed from the side. The upper and lower magnetic pole sections 111 and 113 are attached respectively to the lower surface of the upper horizontal limb and to the upper surface of the lower horizontal limb of the C-shaped yoke 115 in a relationship such that they face each other across the space.

The upper and lower magnetic pole sections 111 and 113 each have a generally short cylindrical shape. The upper and lower magnetic pole sections 111 and 113 each contain the aforementioned main magnetic field magnet section 102, gradient coil section 106 and RF coil section 108.

The upper horizontal limb of the C-shaped yoke and the upper magnetic pole section 111 lie within the hood section 116 of the magnet system 100. The vertical limb of the C-shaped yoke lies within the post section 114 of the magnet system 100. The lower horizontal limb of the C-shaped yoke and the lower magnetic pole section 113 lie within the base section 112 of the magnet system 100.

Thus, the space across which the base section 112 and the hood section 116 face each other forms a space in which the magnetic fields are generated by the main magnetic field magnet section 102, gradient coil section 106 and RF coil section 108.

The base section 112 of the magnet system 100 is provided with the table 500 for placing the subject to be imaged. The table 500 is mounted on the base section 112 so that the longitudinal dimension of the table 500 extends laterally as viewed from the front of the magnet system 110. The surface of the table 500 on which the subject to be imaged is placed is parallel with the upper surface of the base section 112. The table 500 is an embodiment of the support section in accordance with the present invention.

The mounting of the table 500 on the base section 112 is achieved by a pair of mounting mechanisms 300 respectively provided at the right and left end portions of the base section 112 as viewed from the front of the magnet system 100 and the corresponding portions of the lower surface of the table 500. The mounting mechanisms 300 form part of the table driving section 120. The mounting mechanisms 300 represent an embodiment of the position adjusting section in accordance with the present invention.

The mounting mechanisms 300 are formed by link mechanisms. As exemplarily shown in FIG. 3, each link mechanism is constructed by pivotally attaching respective ends of a pair of arms 304 and 304' to a pair of pivots 302 and 302' that are disposed at a predefined interval on the lower surface of the table 500, each pivot being parallel with the longitudinal direction of the table 500, and fixedly attaching respective other ends of the pair of arms 304 and 304' to a pair of pivots 306 and 306' vertically protruding from an end surface of the base section 112 at a predefined interval. The pair of arms 304 and 304' are bent in an L shape.

The pair of pivots 302 and 302' is disposed so that the pivot 302 lies nearer and the pivot 302' lies farther as viewed from the front of the magnet system 100. The pair of pivots 306 and 306' is disposed so that the pivot 306 lies nearer and the pivot 306' lies farther as viewed from the front of the magnet system 100.

The relationship between the pair of pivots 302 and 302' and the pair of pivots 306 and 306' such that the pair of pivots 302 and 302' lies nearer and the pair of pivots 306 and 306' lies farther as viewed from the front of the magnet system 100. Moreover, the pair of pivots 302 and 304' is positioned higher than the upper surface of the base section 112, and the pair of pivots 306 and 306' is positioned lower than the upper surface of the base section 112.

The distance between the pivots 302 and 302' is equal to the distance between the pivots 306 and 306'. Moreover, a line connecting the centers of the pivots 302 and 302' and a line connecting the centers of the pivots 306 and 306' are parallel with each other. Thus, the link mechanism is identical to a so-called parallel-ruler type link mechanism. It should be noted that the arm 304' connecting the pivots 302' and 306' passes between the arm 304 and the base section 112, and makes a downward detour avoiding the pivot 306.

The arms 304 and 304' will be sometimes referred to as a link mechanism hereinbelow. The link mechanism is an embodiment of the link mechanism in accordance with the present invention. The arms 304 and 304' represent an embodiment of the pair of arms in accordance with the present invention.

The pair of pivots 306 and 306' protrudes outward through a slit portion 308 from the inside of the base section 112. The pair of pivots 306 and 306' are torque output axes of actuators provided within the base section 112. The output torque of the actuators keeps the table 500 at a position above the upper surface of the base 112 at a distance, as shown.

The slit portion 308 is an elongated hole extending in parallel with the upper surface of the base section 112. The actuators bearing the pivots 306 and 306' can be linearly moved along the slit portion 308 by a movement mechanism provided within the base section 112. FIG. 3 shows the condition in which the pivots 306 and 306' are moved farthest as viewed from the front of the magnet system 100.

Figure 8:
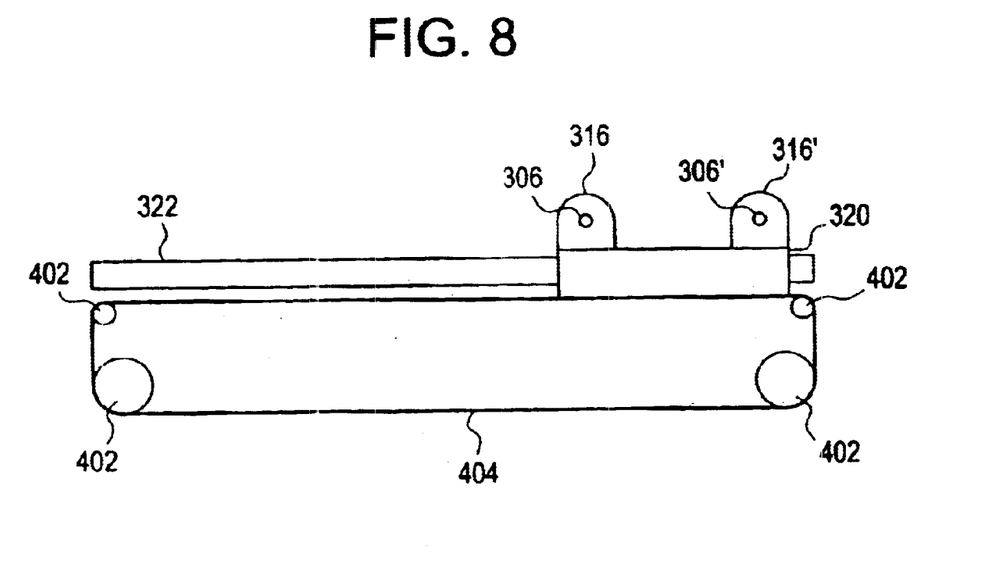
FIG. 8 is a schematic view showing the structure of a table position adjusting mechanism.

FIG. 8 schematically shows an exemplary configuration of the actuators and movement mechanism provided within the base section 112. As shown, actuators 316 and 316' bearing the pivots 306 and 306' are mounted on a carriage 320.

The carriage 320 is movable on a rail 322. The rail 322 runs in parallel with the slit portion 308. The carriage 320 is joined to a portion of a belt 404 traveling around four pulleys 402.

The side of the belt 404 on which the carriage 320 is joined is parallel with the rail 322, and the span of the side is the same as the length of the rail 322. At least one of the four pulleys 402 is driven by a motor (not shown) etc. that is reciprocally rotatable.

Thus, the pivots 306 and 306' of the actuators 316 and 316' can be reciprocally moved along the slit portion 308, and accordingly, the table 500 supported by the pivots 306 and 306' via the link mechanism 304/304' can be reciprocally moved over the base section 112. A portion comprised of the carriage 320, rail 322, pulleys 402 and belt 404 is an embodiment of the movement mechanism in accordance with the present invention.

Figure 9:
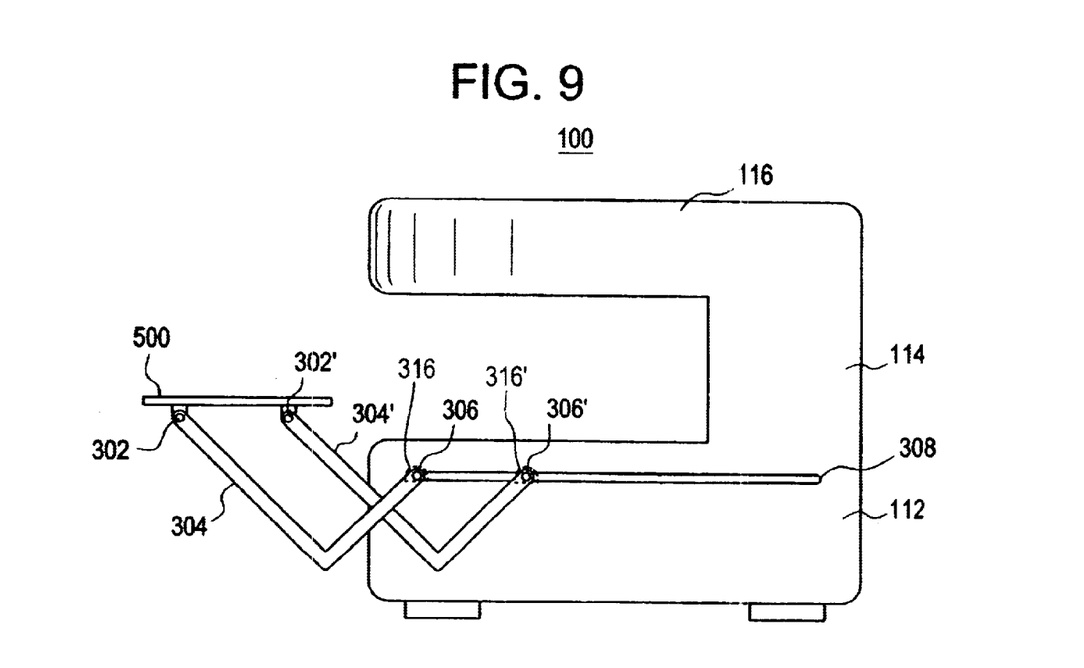
FIG. 9 is a schematic view showing the condition in which the table is pushed out.

FIG. 9 shows the condition in which the table 500 is moved nearest as viewed from the front of the magnet system 100. The positions nearer and farther as viewed from the front of the magnet system 100 will be sometimes referred to simply as those nearer and farther below. FIG. 9 also shows post section 114 and slit portion 308.

As shown in FIG. 9, in this condition, the table 500 is positioned completely out of the space between the base section 112 and the hood section 116. That is, the table 500 is positioned protruding nearer than the front of the magnet system 100 off the base section 112.

In this condition, by rotating the pivots 306 and 306' counterclockwise using the actuators 316 and 316', the link mechanism 304/304' rotates counterclockwise.

The counterclockwise rotation of the link mechanism 304/304' lowers the table 500 while keeping the table 500 in a horizontal orientation. In the condition in which the table 500 is lowered to the lowest position, it comes down near the floor, as exemplarily shown in FIG. 10, which also shows post section 114, slit portion 308, and a pair or pivots 306 and 306'.

Figure 10:
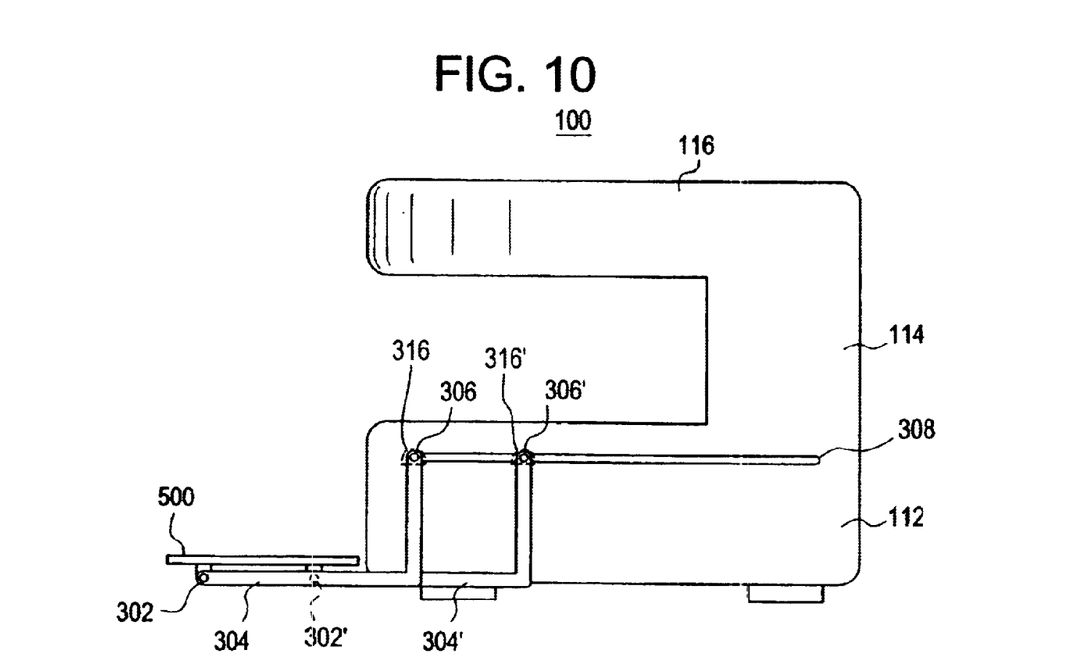
FIG. 10 is a schematic view showing the condition in which the table is lowered.

The link mechanism 304/304' can lower the table 500 near the floor without interfering with the table 500 because the arm 304 bends at a generally right angle. Moreover, since the arm 304' is configured to pass between the arm 304 and base section 112 and make a downward detour avoiding the pivot 306, the table 500 can be lowered from a level higher than the upper surface of the base section 112 to a level near the floor without interference between the arms 304 and 304', and the table 500 can be lifted up from the level near the floor to the level higher than the upper surface of the base section 112.

By appropriately controlling the actuators 316 and 316', the level of the table 500 can be adjusted to any level between the level shown in FIG. 9 and that shown in FIG. 10. By such level adjustment, the level of the table 500 can be set so that the subject to be imaged can easily get on and off the table 500.

For example, the table 500 bearing the subject at the level shown in FIG. 10 is lifted up to the level shown in FIG. 9 by a clockwise rotation of the pivots 306 and 306' by the actuators 316 and 316', and then the table 500 is pulled into the space between the base section 112 and the hood section 116 by movement of the carriage 320. When the carriage 320 moves farthest, the table 500 reaches a fixed position in the space between the base section 112 and the hood section 116, as shown in FIG. 3.

Thus, since the table 500 is mounted on the base section 112 of the magnet system 100 by the mounting mechanism 300, the positional relationship between the table 500 and the base section 112 for receiving it can be always fixed. Moreover, the level of the table 500 can be appropriately adjusted so that the subject to be imaged can easily get on and off the table 500.

Figure 11:
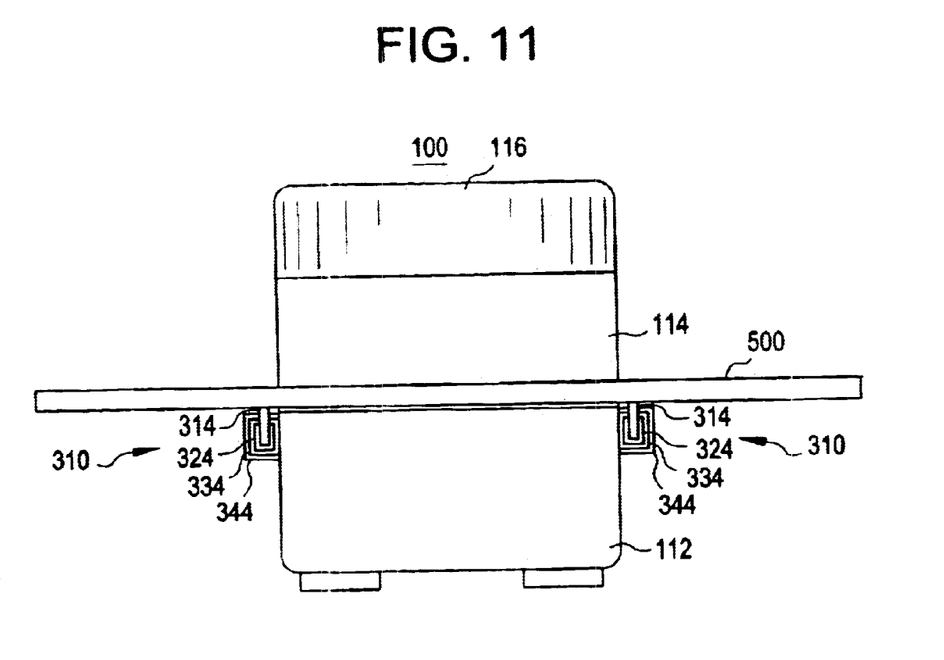
FIG. 11 is a schematic view showing the configuration of a magnet system.
Figure 12:
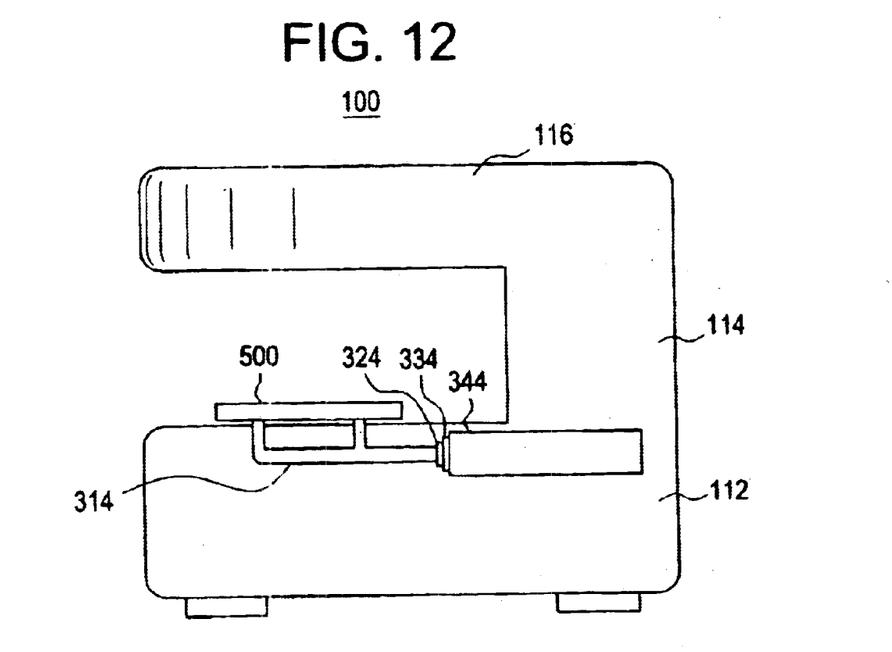
FIG. 12 is a schematic view showing the configuration of the magnet system.
Figure 13:
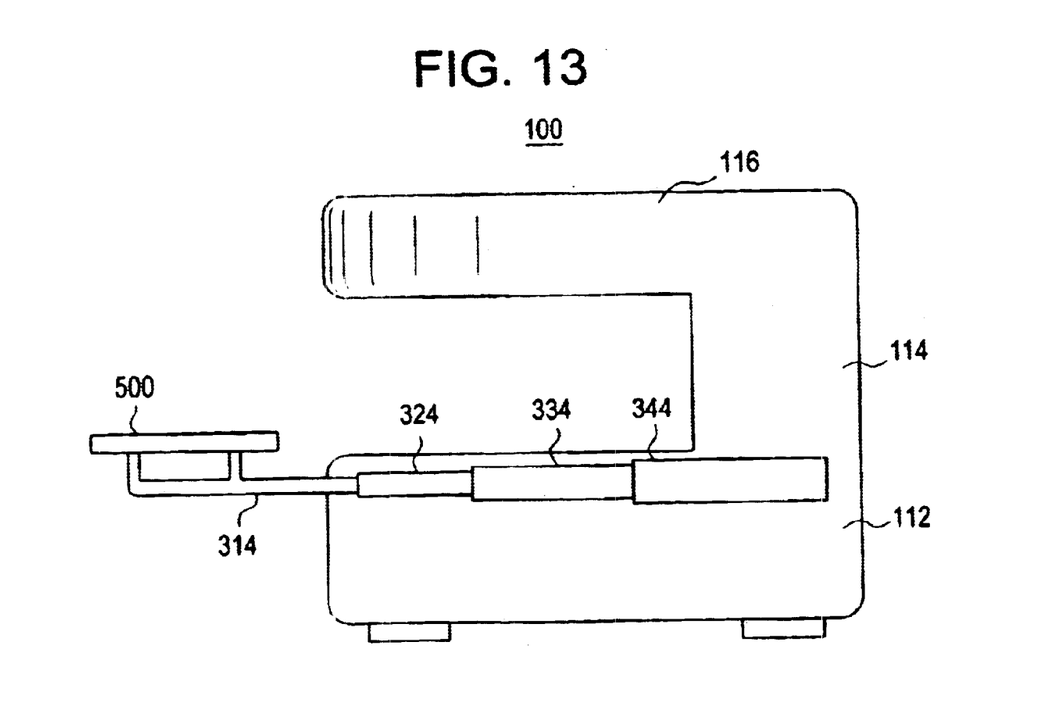
FIG. 13 is a schematic view showing the condition in which the table is pushed out.

FIGS. 11 and 12 schematically show an exemplary configuration in which the table 500 is mounted on the magnet system 100 by a mounting mechanism different from that described above. FIG. 11 is a front elevational view and FIG. 12 is a right side view. Although not shown, a left side view corresponds to a mirror image of FIG. 12. In FIGS. 12 and 13, members other than the mounting mechanism 310 are the same as those shown in FIGS. 2 and 3, and therefore, they are designated by similar reference symbols and explanations thereof will be omitted.

The configuration of the mounting mechanism 310 will now be described with reference to FIG. 12. As shown, the mounting mechanism 310 supports the table 500 by arms 314 from the lower side. The table 500 is kept slightly above the upper surface of the base section 112, as shown. The mounting mechanism 310 forms part of the table driving section 120. The mounting mechanism 310 is an embodiment of the position adjusting section in accordance with the present invention.

A portion of each arm 314 that lies farther as viewed from the front of the magnet system 100 is inserted into a cylinder 324 such that the arm 314 can be slidably moved in the horizontal direction. The cylinder 324 is inserted into a cylinder 334 such that the cylinder 324 can be slidably moved in the horizontal direction. The cylinder 324 is inserted into a cylinder 344 such that the cylinder 334 can be slidably moved in the horizontal direction. The cylinder 344 is fixedly attached to a lateral end portion of the base section 112 as viewed from the front of the magnet system 100. FIG. 12 shows the condition in which the arm 314 and the cylinders 324 and 334 are inserted most deeply into the respective receiving cylinders.

The cylinders 324, 334 and 344 incorporate a mechanism for pushing and pulling the respective inner portions of the arm and cylinders by using for example, hydraulic pressure. Thus, a portion comprised of the arm 314 and the cylinders 324, 334 and 344 forms an arm as a whole that is extendable in the horizontal direction. The portion comprised of the arm 314 and the cylinders 324, 334 and 344 will be sometimes referred to as an extendable arm hereinbelow. The extendable arm is an embodiment of the extendable arm in accordance with the present invention.

FIG. 13 shows the condition in which the extendable arm is extended most. As shown, in this condition, the table 500 is positioned completely out of the space between the base section 112 and the hood section 116. That is, the table 500 is positioned protruding nearer than the front of the magnet system 100 off the base section 112. Thus, the subject to be imaged can get on and off the table 500 without interference from the hood section 116 of the magnet system 100.

The table 500 bearing the subject in the condition shown in FIG. 13 is pulled into the space between the base section 112 and the hood section 116 by a retracting operation of the extendable arm. In the condition in which the extendable arm is retracted most, the table 500 reaches a fixed position in the space between the base section 112 and the hood section 116, as shown in FIG. 12.

Thus, since the table 500 is mounted on the base section 112 of the magnet system 100 by the mounting mechanism 310, the positional relationship between the table 500 and the base section 112 for receiving it can be always fixed.

Figure 14:
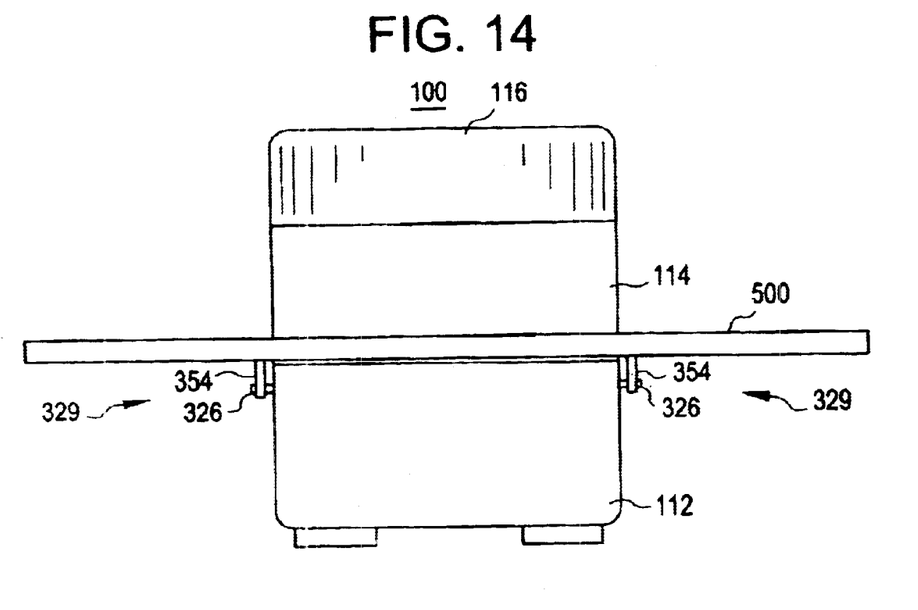
FIG. 14 is a schematic view showing the configuration of a magnet system.
Figure 15:
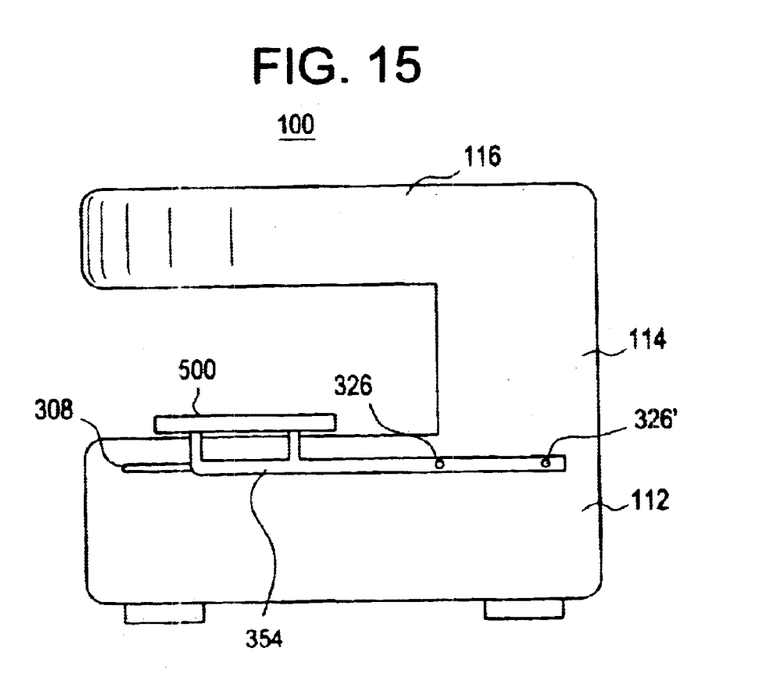
FIG. 15 is a schematic view showing the configuration of the magnet system.

FIGS. 14 and 15 schematically show an exemplary configuration in which the table 500 is mounted on the magnet system 100 by a mounting mechanism different from those described above. FIG. 14 is a front elevational view and FIG. 15 is a right side view. Although not shown, a left side view corresponds to a mirror image of FIG. 15. In FIGS. 14 and 15, members other than the mounting mechanism 329 are the same as those shown in FIGS. 2 and 3, and therefore, they are designated by similar reference symbols and explanations thereof will be omitted.

The configuration of the mounting mechanism 329 will now be described with reference to FIG. 15. As shown, the mounting mechanism 329 supports the table 500 by arms 354 from the lower side. The table 500 is kept slightly above the upper surface of the base section 112. The mounting mechanism 329 forms part of the table driving section 120. The mounting mechanism 329 is an embodiment of the position adjusting section in accordance with the present invention. The arm 354 is an embodiment of the support arm in accordance with the present invention.

A portion of each arm 354 that lies farther as viewed from the front of the magnet system 100 is fixedly attached to pivots 326 and 326'. The pivots 326 and 326' are disposed so that the pivot 326 lies nearer and the pivot 326' lies farther as viewed from the front of the magnet system 100.

The pivots 326 and 326' protrude outward through a slit portion 308 from the inside of the base section 112. The pivots 326 and 326' are supported by bearing members provided within the base section 112.

The slit portion 308 is an elongated hole extending in parallel with the upper surface of the base section 112. The bearing members bearing the pivots 326 and 326' are linearly movable along the slit portion 308 by a movement mechanism provided within the base section 112. FIG. 15 shows the condition in which the pivots 326 and 326' are moved farthest as viewed from the front of the magnet system 100.

Figure 16:
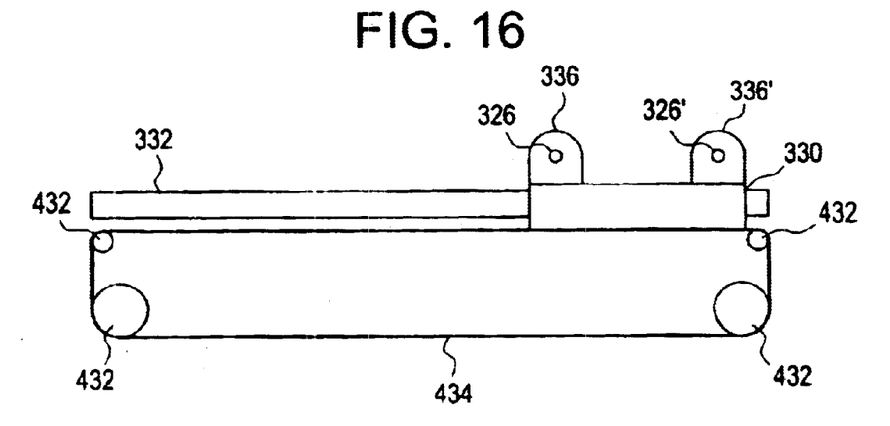
FIG. 16 is a schematic view showing the structure of the table position adjusting mechanism.

FIG. 16 schematically shows an exemplary configuration of the bearing members and movement mechanism provided within the base section 112. As shown, bearing members 336 and 336' bearing the pivots 326 and 326' are mounted on a carriage 330.

The carriage 330 is movable on a rail 332. The rail 332 runs in parallel with the slit portion 308. The carriage 330 is joined to a portion of a belt 434 traveling around four pulleys 432.

The side of the belt 434 on which the carriage 330 is joined is parallel with the rail 332, and the span of the side is the same as the length of the rail 332. At least one of the four pulleys 432 is driven by a motor (not shown) etc. that is reciprocally rotatable.

Thus, the pivots 326 and 326' can be reciprocally moved along the slit portion 308, and accordingly, the table 500 supported by the pivots 326 and 326' via the arm 354 can be reciprocally moved over the base section 112. FIGS. 15 and 16 show the condition in which the arm 354 is moved farthest as viewed from the front of the magnet system 100. A portion comprised of the carriage 330, rail 332, pulleys 432 and belt 434 is an embodiment of the movement mechanism in accordance with the present invention.

Figure 17:
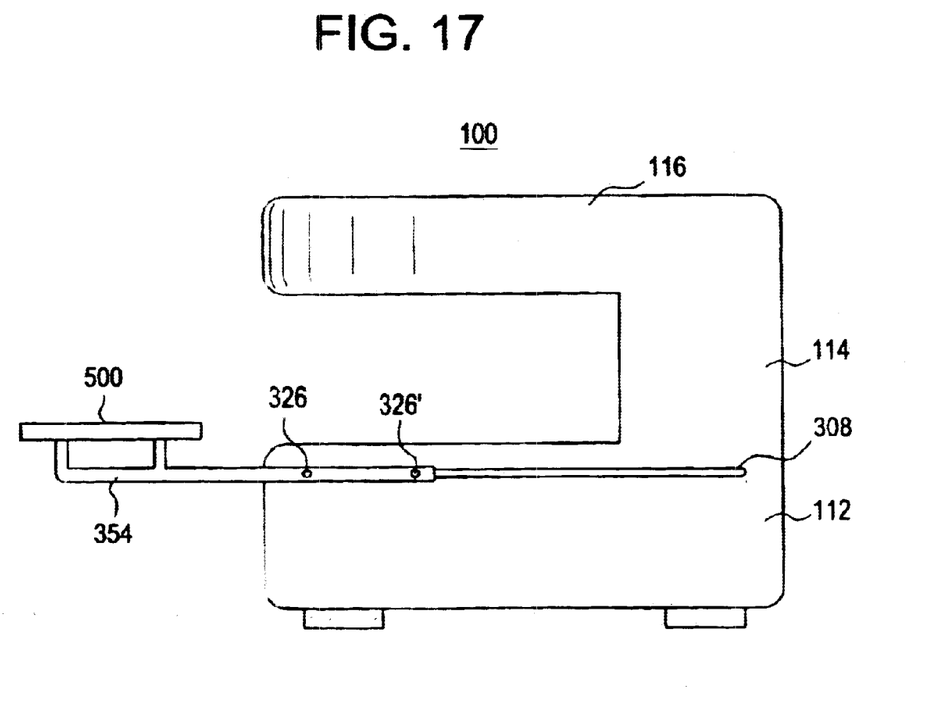
FIG. 17 is a schematic view showing the condition in which a table is pushed out

FIG. 17 shows post section 114 and slit portion 308. FIG. 17 also shows the condition in which the table 500 is moved nearest as viewed from the front of the magnet system 100. As shown, in this condition, the table 500 is positioned completely out of the space between the base section 112 and the hood section 116. That is, the table 500 is positioned protruding nearer than the front of the magnet system 100 off the base section 112. Thus, the subject to be imaged can get on and off the table 500 without interference from the hood section 116 of the magnet system 100.

The table 500 bearing the subject in the condition shown in FIG. 17 is pulled into the space between the base section 112 and the hood section 116 by a retracting operation of the arm 354. In the condition in which the arm is retracted most, the table 500 reaches a fixed position in the space between the base section 112 and the hood section 116, as shown in FIG. 15.

Thus, since the table 500 is mounted on the base section 112 of the magnet system 100 by the mounting mechanism 300, the positional relationship between the table 500 and the base section 112 for receiving it can be always fixed.

While the present invention has been described with reference to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above but all that fall within the scope of the appended claims.

Many widely different embodiments of the invention may be constructed without departing from the spirit and the scope of the present invention. It should be understood that the present invention is not limited to the specific embodiments described in the specification, except as defined in the appended claims.

What is claimed is:

1. A magnetic resonance imaging apparatus magnet system that has a space for receiving a subject to be imaged and generates a static magnetic field, a gradient magnetic field and a high frequency magnetic field in said space, comprising:

a base section having a horizontal plane on its top;

a post section provided on one side of said base section and extending upright beyond said horizontal plane;

a hood section supported by said post section, facing said horizontal plane across said space, wherein said base section faces said hood section, and the space for imaging the subject is formed between said base section and said hood section;

a support section horizontally supporting the subject to be imaged; and a position adjusting section provided between said base section and said support section, wherein said position adjusting section moves said support section forward/backward between a position above said horizontal plane and a position off said horizontal plane on the other side of said base section while keeping said support section at a level higher than said horizontal plane, and moves said support section upward/downward between a position higher than said horizontal plane and a position lower than said horizontal plane at said position off said horizontal plane, wherein said support section is coupled via said position adjusting section to said base section that faces said hood section to form the space in which the subject is imaged.

2. The magnetic system of claim 1, wherein the position adjusting section comprises:

a pair of link mechanisms respectively provided between two positions of said support section along a direction parallel with said horizontal plane and perpendicular to the direction of said forward/backward movement and the corresponding end portions of said base section, said link mechanism being pivotally rotatable relative to said base section; and a movement mechanism moving a portion of said pair of link mechanisms adjacent to said base section in the direction of said forward/backward movement.

3. The magnet system of claim 2, wherein each member of said pair of link mechanisms comprises:

a pair of arms configured to avoid mutual interference involved in said pivotal rotation.

4. The magnet system of claim 1, wherein said static magnetic field is generated by permanent magnets.

5. A magnetic resonance imaging apparatus having:

a magnet system that has a space which receives a subject to be imaged, wherein said magnet system generates a static magnetic field, a gradient magnetic field and a high frequency magnetic field in said space; and image producing means for producing an image based on magnetic resonance signals acquired through said magnet system, characterized in that said magnet system comprises:

a base section having a horizontal plane on its top;

a post section provided on one side of said base section and extending upright beyond said horizontal plane;

a hood section supported by said post section, facing said horizontal plane across said space, wherein said base section faces said hood section, and the space for imaging the subject is formed between said base section and said hood section;

a support section horizontally supporting the subject to be imaged; and a position adjusting section provided between said base section and said support section, wherein said position adjusting section moves said support section forward/backward between a position above said horizontal plane and a position off said horizontal plane on the other side of said base section while keeping said support section at a level higher than said horizontal plane, and moving said support section upward/downward between a position higher than said horizontal plane and a position lower than said horizontal plane at said position off said horizontal plane, wherein said support section is coupled via said position adjusting section to said base section that faces said hood section to form the space in which the subject is imaged.

6. The magnetic resonance imaging apparatus of claim 5, wherein the position adjusting section comprises:

a pair of link mechanisms respectively provided between two positions of said support section along a direction parallel with said horizontal plane and perpendicular to the direction of said forward/backward movement and the corresponding end portions of said base section, said link mechanism being pivotally rotatable relative to said base section; and a movement mechanism moving a portion of said pair of link mechanisms adjacent to said base section in the direction of said forward/backward movement.

7. The magnetic resonance imaging apparatus of claim 6, wherein each member of said pair of link mechanisms comprises:

a pair of arms configured to avoid mutual interference involved in said pivotal rotation.

8. The magnetic resonance imaging apparatus of claim 5, wherein said static magnetic field is generated by permanent magnets.

9. The magnetic resonance imaging apparatus of claim 5, wherein said base section, post section, and hood section include a C-shaped yoke.

10. A magnetic resonance imaging apparatus having:

a magnet system that has a space which receives a subject to be imaged, wherein said magnet system generates a static magnetic field, a gradient magnetic field and a high frequency magnetic field in said space; and image producing means for producing an image based on magnetic resonance signals acquired through said magnet system, wherein said magnet system comprises:

a base section having a horizontal plane on its top;

a post section provided on one side of said base section and extending upright beyond said horizontal plane;

a hood section supported by said post section, facing said horizontal plane across said space, wherein said base section faces said hood section, and the space for imaging the subject is formed between said base section and said hood section;

a support section horizontally supporting the subject to be imaged; and a position adjusting section provided between said base section and said support section, wherein said position adjusting section moves said support section forward/backward between a position above said horizontal plane and a position off said horizontal plane on the other side of said base section while keeping said support section at a level higher than said horizontal plane, wherein said support section is coupled via said position adjusting section to said base section that faces said hood section to form the space in which the subject is imaged.

11. The magnetic resonance imaging apparatus of claim 10, wherein said position adjusting section comprises:

a pair of extendable arms respectively provided between two positions of said support section along a direction parallel with said horizontal plane and perpendicular to the direction of said forward/backward movement and the corresponding end portions of said base section, said extendable arms being capable of extending relative to said base section.

12. The magnetic resonance imaging apparatus of claim 10, wherein the position adjusting section comprises:

a pair of support arms respectively provided between two positions of said support section along a direction parallel with said horizontal plane and perpendicular to the direction of said forward/backward movement and the corresponding end portions of said base section, and a movement mechanism moving a portion of said pair of support arms adjacent to said base section in the direction of said forward/backward movement.

13. The magnetic resonance imaging apparatus of claim 10, wherein said static magnetic field is generated by permanent magnets.

* * * * *